United States Patent [19]

Nakane

[11] Patent Number: 4,526,901

[45] Date of Patent: Jul. 2, 1985

[54] 7-OXABICYCLOHEPTANE SUBSTITUTED OXAMIDE PROSTAGLANDIN ANALOGS AND THEIR USE IN TREATING THROMBOLYTIC DISEASE

[75] Inventor: Masami Nakane, Hopewell, N.J.

[73] Assignee: E. R. Squibb & Sons, Inc., Princeton, N.J.

[21] Appl. No.: 573,992

[22] Filed: Jan. 26, 1984

[51] Int. Cl.³ .................. A61K 31/557; C07D 307/00
[52] U.S. Cl. ...................................... 514/469; 549/463
[58] Field of Search ......................... 549/463; 424/285

[56] References Cited

U.S. PATENT DOCUMENTS

| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292  8/1982  European Pat. Off.
2039909  8/1980  United Kingdom Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted oxamide prostaglandin analogs are provided having the structural formula

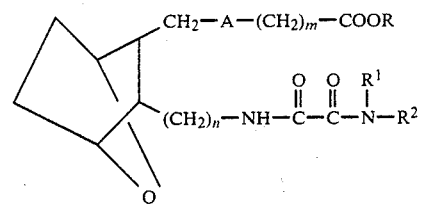

and including all stereoisomers thereof.

The compounds are cardiovascular agents useful, for example, in the treatment of thrombolytic disease.

11 Claims, No Drawings

7-OXABICYCLOHEPTANE SUBSTITUTED OXAMIDE PROSTAGLANDIN ANALOGS AND THEIR USE IN TREATING THROMBOLYTIC DISEASE

DESCRIPTION OF THE INVENTION

The present invention relates to 7-oxabicycloheptane substituted oxamide prostaglandin analogs which are cardiovascular agents useful, for example, in the treatment of thrombolytic disease. These compounds have the structural formula

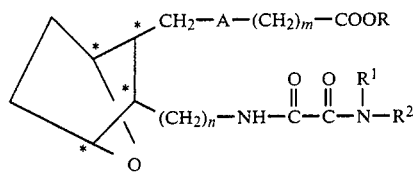

and including all stereoisomers thereof, wherein
A is $CH=CH$ or $(CH_2)_2$;
m is 1 to 8;
n is 1 to 5;
R is H, lower alkyl or alkali metal; and
$R^1$ and $R^2$ may be the same or different and are hydrogen, lower alkyl, aryl, aralkyl, or cycloalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent such as F, Br, Cl or I, or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as hexyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "halogen" or "halo" as used herein refers to chlorine, bromine, fluorine or iodine with chlorine being preferred.

The terms "$(CH_2)_m$", and "$(CH_2)_n$" include a straight or branched chain radical having from 1 to 8 carbons in the normal chain in the case of "$(CH_2)_m$" and 1 to 5 carbons in the normal chain in the case of "$(CH_2)_n$" and may contain one or more lower alkyl substituents. Examples of $(CH_2)_m$, and $(CH_2)_n$ groups include $CH_2$, $CH_2CH_2$, $(CH_2)_3$, $(CH_2)_4$, $(CH_2)_5$, $(CH_2)_6$, $(CH_2)_7$,

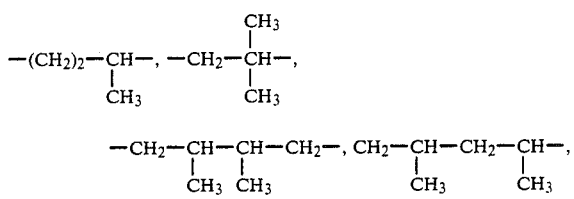

and the like.

Preferred are those compounds of formula I wherein A is $(CH_2)_2$ or $CH=CH$, m is 2 to 4, R is H, n is 1 to 5, $R^1$ is hydrogen and $R^2$ is phenyl, benzyl or lower alkyl.

The various compounds of the invention may be prepared as outlined below.

A. n is 1

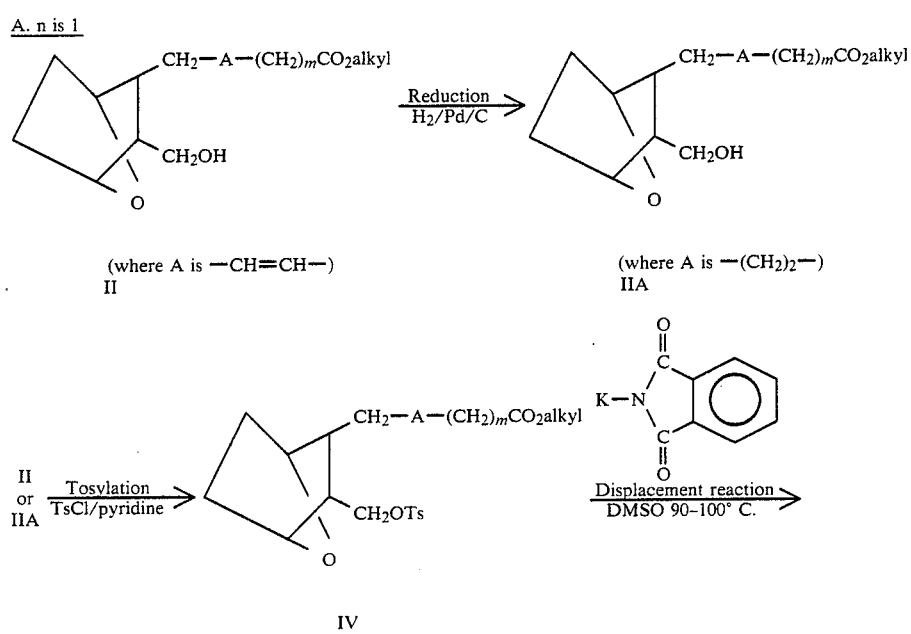

IV

-continued
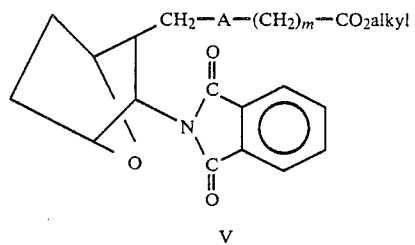
V
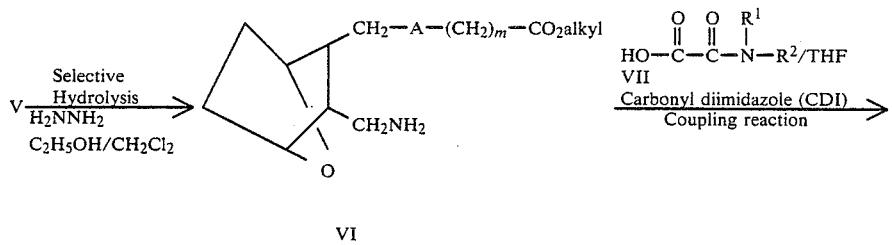
VI
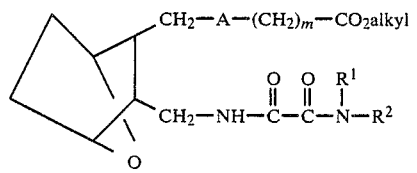
IA
B. Where n is 2 to 5
II
or  Collins oxidation →
IIa
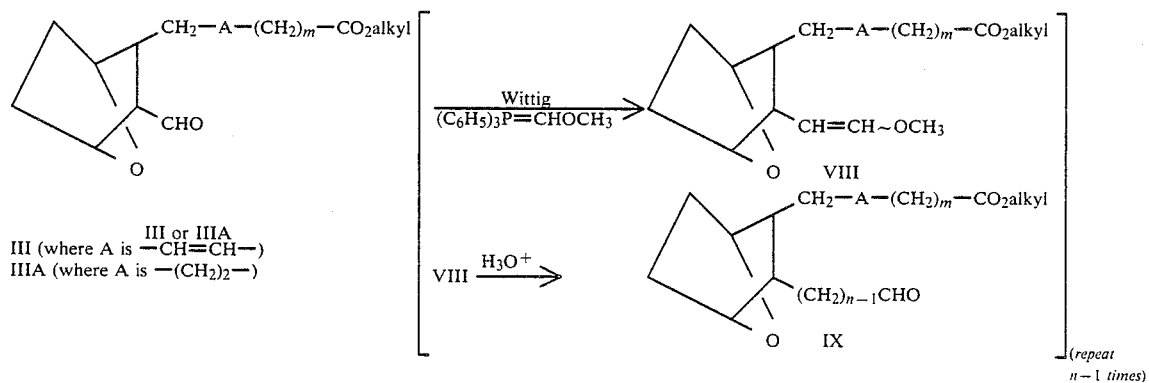
III (where A is —CH=CH—)
IIIA (where A is —(CH$_2$)$_2$—)
*(repeat n−1 times)*
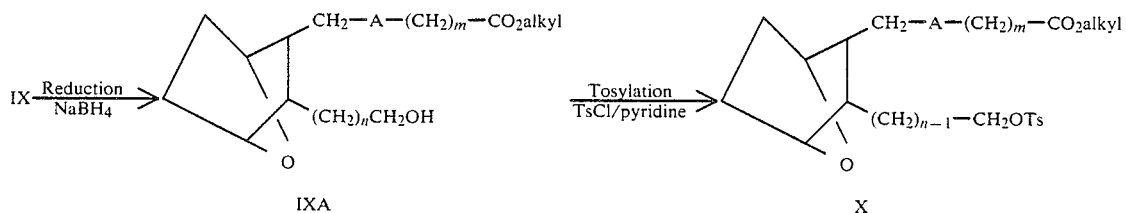
IXA          X -continued

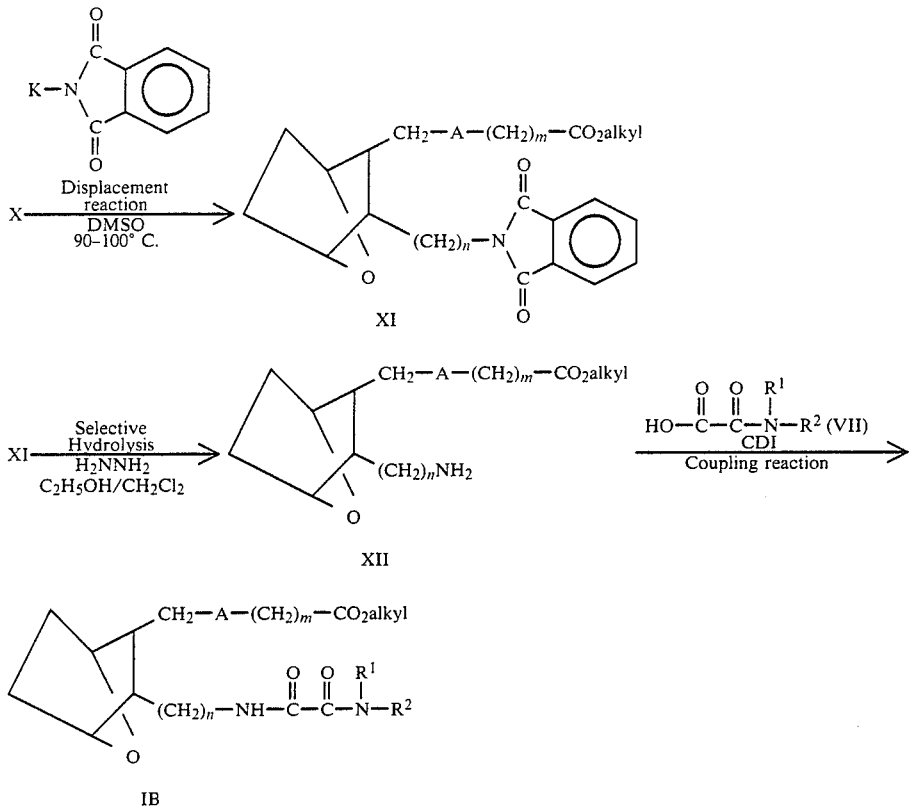

As seen in reaction sequence "A", compounds of the invention where n is 1, that is

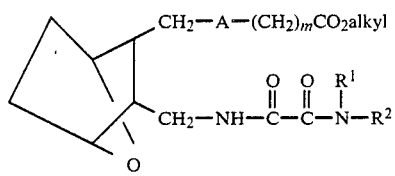

are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

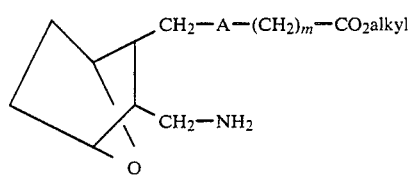

The amine VI is then subjected to a CDI coupling reaction by reacting VI with acid VII

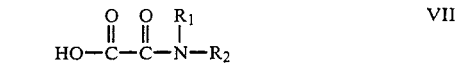

in the presence of an inert organic solvent such as tetrahydrofuran and carbonyl diimidazole under an inert atmosphere, such as argon, employing a molar ratio of VI:VII of within the range of from about 1:1 to about 1:1.2, to form the oxamide ester compound of the invention IA

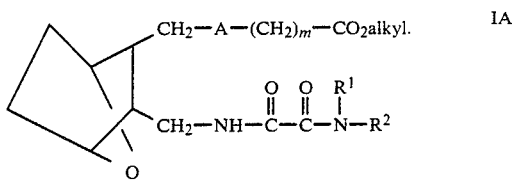

The reaction sequence identified as "B" is employed to prepare comounds of the invention wherein n is 2 to 5, that is,

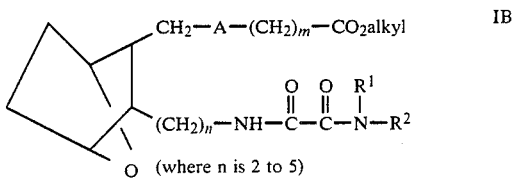

Compound II or IIA is used to form the aldehyde III (where A is —CH=CH—) or IIIA (where A is —(CH₂)₂). Thus, to form aldehyde III where A is —CH═CH—, comound II is subjected to a Collins oxidation, for example, by reacting II with chromium trioxide in pyridine. To form the aldehyde IIIA (where A is (CH$_2$)$_2$) compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$). The aldehyde III or IIIA is used to prepare aldehyde IX (where n is 2–5) by carrying out a homologation sequence, such as a Wittig reaction with (C$_6$H$_5$)$_3$P═CHOMe followed by hydrolysis, (n−1) times. The aldehyde IX (where n is 2–5) is then carried on to compounds of this invention where n is 2–5, that is

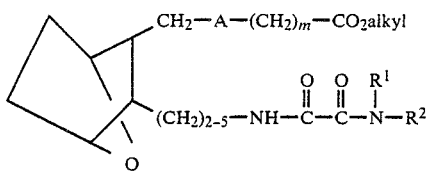
IB by reducing aldehyde IX by reacting with a reducing agent such as sodium borohydride to form alcohol IXA

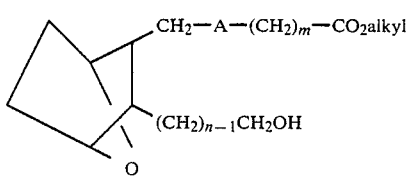
IXA tosylating aldehyde IXA as described above to form the tosylate X which is subjected to a displacement reaction with potassium phthalimide as described above to form the phthalimide XI. Phthalimide XI is then made to undergo selective hydrolysis as described above to form the amine XII

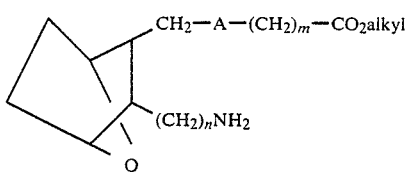
XII which is then reacted with acid VII in a CDI coupling reaction as described above to form the oxamide ester compound of the invention IB

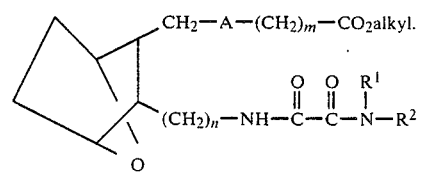
IB

The esters IA and IB can be converted to the free acid, that is, to

IC (A is —CH═CH—)
ID (A is (CH$_2$)$_2$)

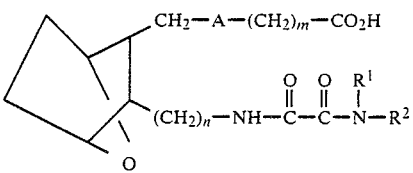

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IC and ID.

The starting acid compound VII

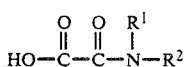
VII may be prepared by reacting dimethyl oxalate

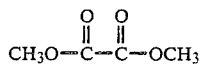
A with the appropriate amine B

B in the presence of an inert organic solvent such as methanol or ethanol, to form the amide C

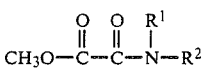
C which is then hydrolyzed in the presence of an alkali metal hydroxide such as LiOH to form the acid VII.

Where each of R$^1$ and R$^2$ is hydrogen, the starting oxamic acid

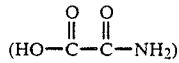

is known in the art.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

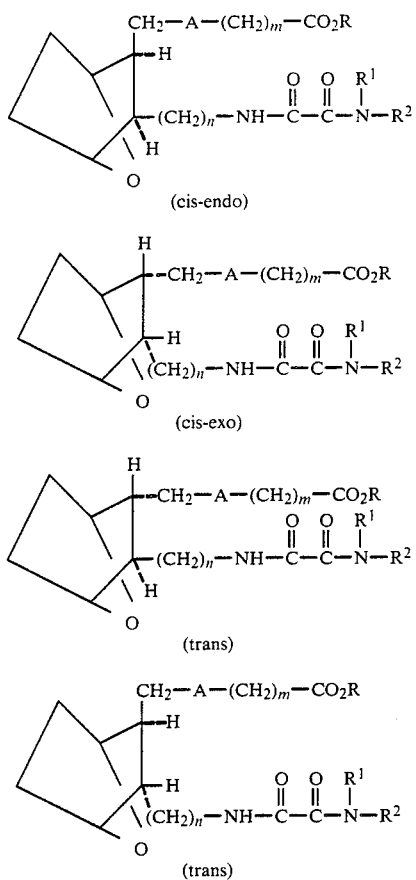

(cis-endo)

(cis-exo)

(trans)

(trans)

The nucleus in each of the compounds of the invention is depicted as

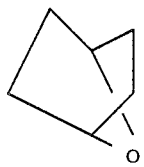

for matter of convenience; it will also be appreciated that the nucleus in the compounds of the invention may be depicted as

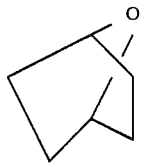

The compounds of this invention are cardiovascular agents useful as platelet aggregation inhibitors, such as in inhibiting arachidonic acid-induced platelet aggregation, e.g., for treatment of thrombolytic disease, such as coronary of cerebral thromboses and for inhibiting bronchoconstriction associated with asthma. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of this invention.

EXAMPLE 1

[1β,2α(5Z),3α,4β]-7-[3-[[[Oxo(phenylamino)acetyl]amino]methyl]-7-oxabicyclo[2.2.1]hept-2-yl]-5-heptenoic acid, methyl ester

A.

[1β,2α(5Z),3α,4β]-7-[3-(Tosyloxymethyl)-7-oxabicyclo[2.2.1]hept-2-yl]-5-heptenoic acid, methyl ester Tosyl chloride (4.256 g, 22.4 mmol) dissolved in $CH_2Cl_2$ (30 ml) was added dropwise to a magnetically stirred solution of [1β,2α(5Z),3α,4β]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/$H_2O$ and stirred for 30 minutes. The products were extracted with EtOAc (80 ml×3). The combined EtOAc layers were washed with 3N—HCl (40 ml×3), saturated $NaHCO_3$, brine and dried over $MgSO_4$. Filtration and evaporation of solvent gave a white solid, which was crystallized from isopropyl ether to give the corresponding title tosylate in the form of needle crystals (4.23 g, 89%), m.p. 68°-70° C.

B.

[1β,2α(5Z),3α,4β]-7-[(3-(Aminomethyl)-7-oxabicyclo[2.2.1]hept-2-yl]-5-heptenoic acid, methyl ester The title A tosylate was subjected to a Gabriel synthesis to form the corresponding amino compound as described below.

A mixture of title A tosylate (2.86 g, 6.78 mmol) and potassium phthalimide [2.23 g, 12.2 mmol, which had been purified by boiling 5 g with acetone (9 ml) for 15 minutes, filtering hot, washing with 5 ml acetone and drying 6 hours at 100° C. in vacuo] in DMSO (25 ml) was heated at 90°-100° C. for 2 hours. After cooling, water (30 ml) was added. Some material precipitated out. The mixture was filtered thorugh Celite. The filtrate was extracted with ether (3×40 ml). The Celite pad was washed with ether (4×2 ml). The combined ether solutions were washed with water (2×40 ml), dried ($MgSO_4$), filtered and freed of solvent in vacuo leaving 0.87 g of white solid. The Celite filter pad was suspended in ether (40 ml), heated and filtered. This process was repeated. The ether solution was washed with water (2×30 ml), dried and combined with the other material obtained to give 2.66 g of white solid (98.8%). This was recrystallized from isopropyl ether to give corresponding phthalide (2.04 g, 75.8%). TLC: silica gel, Et$_2$O-hexane 2:1 UV and vanillin R$_f$=0.35.

The above phthalimide (2.04 g, 5.14 mmol) was dissolved in distilled CH$_2$Cl$_2$ (9 ml) and dry distilled EtOH (40 ml) in an argon atmosphere. Anhydrous hydrazine (0.325 ml, 10.3 mmol) was added and the mixture was left stirring overnight at room temperature. The precipitated solid was removed by filtration and washed with more CH$_2$Cl$_2$. The filtrate was taken to dryness in vacuo leaving a very viscous material (1.97 g). One half of this material was chromatographed on silica gel 60 (50 g), eluting with 4–6% methanol in CH$_2$Cl$_2$ containing 0.2% NH$_4$OH to give amine B (256 mg, 37%). TLC: silica gel, 15% MeOH in CH$_2$Cl$_2$+NH$_4$OH (3 drops/10 ml), UV and vanillin R$_f$=0.42.

C. Methyl N-phenyloxamate

A mixture of dimethyl oxalate (11.8 g, 0.1M) and aniline (9.3 g, 0.1M) in MeOH (20 ml) was heated under reflux for 12 hours. After cooling to 0° C., white solid (14.8 g) was removed by filtration. This material was partially dissolved in acetone. Insoluble materil was removed by filtration. The filtrate was taken to dryness in vacuo. The white solid residue was crystallized from methanol to give title C compound as white crystals (6.9 g, 39%), m.p. 109°–112° C. TLC, silica gel, 1% MeOH in CH$_2$Cl$_2$, UV+PMA R$_f$=0.63.

D. N-Phenyloxamic acid

Title C compound (1.79 g, 10 mmol) was dissolved in distilled THF (50 ml) and treated with 1N LiOH solution (20 ml). The mixture was left standing overnight at room temperature. White solid material had precipitated from the reaction mixture. Water (20 ml) was added and the mixture was then poured into ether (50 ml). The organic layer that separated was extracted with a 0.5N NaOH (30 ml). The combined aqueous layers were washed with ether (50 ml) and then acidified to pH 1–2 with concentrated HCl. After saturation with NaCl, the product was extracted into EtOAc (2×50 ml). The combined EtOAc extracts were washed with saturated NaCl solution, dried (MgSO$_4$) and freed of solvent in vacuo leaving a white solid (1.52 g). This was crystallized from toluene-isopropyl alcohol to give title D compound (1.13 g, 68%), m.p. 152°–153° C.

E. [1β,2α(5Z), 3α,4β]-7-[3-[[[Oxo(phenylamino)acetyl]amino]methyl]-7-oxabicyclo[2.2.1]hept-2-yl]-5-heptenoic acid, methyl ester Title D compound (165 mg, 1 mmol) was dissolved in THF (8 ml) in an argon atmosphere and the solution was cooled in an ice bath. Carbonyl diimidazole (162 mg, 1 mmol) was added. The mixture was stirred cold for 1 hour and at room temperature for 1 hour. The mixture was then again cooled in an ice bath and a solution of title B amine (267 mg, 1 mmol) in THF (2 ml) was added. The reaction was left stirring overnight at room temperature. The solvent was removed in vacuo and the residue was partially dissolved in CH$_2$Cl$_2$ (30 ml). This was washed with 1N HCl (15 ml), 1N NaOH (15 ml) and H$_2$O (15 ml), dried (MgSO$_4$), and freed of solvent in vacuo leaving a mixture of solid and oil (307 mg). TLC indicated this was a mixture of 2 major and several minor products. This was chromatographed on silica gel 60 (25 g) eluting with 3% MeOH in CH$_2$Cl$_2$ to give title E methyl ester as a white solid (106 mg, 25%). The product was characterized by M.S., 270 MHz NMR and $^{13}$C NMR. TLC—silica gel, 5% MeOH in CH$_2$Cl$_2$, UV and vanillin. Title E compound, R$_f$=0.77.

EXAMPLE 2

[1β,2α(5Z), 3α,4β]-7-[3-[[[Oxo(phenylamino)acetyl]amino]methyl]-7-oxabicyclo[2.2.1]hept-2-yl]-5-heptenoic acid The Example 1 methyl ester (198 mg, 0.48 mmol) was dissolved in distilled THF (15 ml) and water (4 ml) in an argon atmosphere. 1N LiOH solution (4.8 ml) was added and the mixture was stirred at room temperature for 2.75 hours. 1N HCl solution was added (pH 5) followed by solid NaCl. The layers were separated. The aqueous layer was extracted with CHCl$_3$ (3×25 ml). The combined organic layers (THF and CHCl$_3$) were washed with saturated NaCl solution (2×25 ml), dried (MgSO$_4$) and freed of solvent in vacuo leaving a yellowish solid (172 mg). This was recrystallized from isopropyl alcohol to give title compound, 90 mg (47%), m.p. 153°–155° C. TLC: silica gel, 5% MeOH in CH$_2$Cl$_2$ UV and vanillin. R$_f$=0.23.

Anal Calcd for C$_{22}$H$_{28}$O$_5$N$_2$: C, 65.98; H, 7.05; N, 7.00. Found: C, 65.81; H, 7.03; N, 6.78.

EXAMPLE 3

[1β,2α(5Z),3β,4β]-7-[3-[[[Oxo(phenylamino)acetyl]amino]methyl]-7-oxabicyclo[2.2.1]hept-2-yl]-5-heptenoic acid, methyl ester Following the procedure of Example 1, except substituting [1β,2α(5Z), 3β,4β]-7-[3-(hydroxymethyl)-7-oxabicyclo[2.2.1]hept-2-yl]-5-heptenoic acid, methyl ester prepared as described in U.S. Pat. No. 4,143,054 for [1β,2α(5Z), 3α,4β]-7-[3-(hydroxymethyl)-7-oxabicyclo[2.2.1]hept-2-yl]-5-heptenoic acid, methyl ester, the title compound is obtained.

EXAMPLE 4

[1β,2α(5Z), 3β,4β]-7-[3-[[[Oxo(phenylamino)acetyl]amino]methyl]-7-oxabicyclo[2.2.1]hept-2-yl]-5-heptenoic acid Following the procedure of Example 2 except substituting Example 3 methyl ester for Example 1 methyl ester, the title compound is obtained.

EXAMPLE 5

(1β,2β,3α,4β)-7-[3-[[[Oxo(phenylamino)acetyl]amino]methyl]-7-oxabicyclo[2.2.1]hept-2-yl]-5-heptanoic acid

A. (1β,2β,3β,4β)-7-[3-(Hydroxymethyl)-7-oxabicyclo[2.2.1]hept-2-yl]heptanoic acid To 800 mg (3.0 mmole) of the [1β,2β(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. (1β,2β, 3α,4β)-7-[3-[[[Oxo(phenylamino)acetyl]amino]methyl]-7-oxabicyclo[2.2.1]hept-2-yl]heptanoic acid Following the procedure of Examples 1 and 2 except substituting the Part A alcohol for [1β,2α(5Z),3α,4β]-7-[3-(hydroxymethyl)-7-oxabicyclo[2.2.1]hept-2-yl]-5-heptenoic acid, methyl ester, the title product is obtained.

EXAMPLE 6

1β,2α(5Z), 3α,4β]-7-[3-[[[Oxo(phenylamino)acetyl]amino]ethyl]-7-oxabicyclo[2.2.1]hept-2-yl]-5-heptenoic acid

A. [1β,2α(5Z), 3α,4β]-7-[[3-(2-Oxo)ethyl]-7-oxabicyclo[2.2.1]hept-2-yl]-5-heptenoic acid, methyl ester Into a dry 1000 ml round bottom 3-necked flask containing a stir bar was added 12.9 g (37.7 mmoles)methoxymethyltriphenylphosphonium chloride ((CH$_6$H$_5$)$_3$P$^+$—CH$_2$OCH$_3$Cl$^-$) and 235 ml distilled toluene (stored over molecular sieves). The resulting suspension was stirred in an ice bath under argon until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z), 3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH$_4$Cl and extracted with ether (4×200 ml). The combined ether phases were washed with NaCl, saturated solution, and dried (MgSO$_4$) and concentrated to yield a yellow oil in a white crystalline solid (phosphine oxide). The white solid was triturated out with EtOAc. The filtrate was purified by an LP-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethenyl-7-oxabicyclo[2.2.1]hept-2-yl]-5-heptenoic acid, methyl ester, and (C) [1β,2α(5Z),-3α,4β]-7-[3-(2,2-dimethoxy)ethyl-7-oxabicyclo[2.2.1]hept-2-yl]-5-heptenoic acid, methyl ester.

Compounds (B) and (C) were each treated with trifluoroacetic acid to convert each to compound (A).

B. [1β,2α(5Z),3α,4β]-7-[3-(Hydroxyethyl)-7-oxabicyclo[2.2.1]hept-2-yl]-5-heptenoic acid, methyl ester A solution of 266 mg (1 mmol) [1β,2α(5Z),3α,4β]-7-[3(2-oxo)ethyl-7-oxabicyclo[2.2.1]hept-2-yl]-5-heptenoic acid, methyl ester in 16 ml of methanol is cooled to 0° C. To this stirred solution is added 40 mg of NaBH$_4$ (1.04 mmol) in one portion. After stirring for 20 minutes, the reaction mixture is poured into 70 ml saturated NH$_4$Cl solution and is extracted with ethyl acetate (3×40 ml). The combined ethyl acetate extracts are dried over MgSO$_4$, filtered and concentrated in vacuo to give the title compound.

C. [1β,2α(5Z),3α,4β]-7-[3-[[[Oxo(phenylamino)acetyl]amino]ethyl]-7-oxabicyclo[2.2.1]hept-2-yl]-5-heptenoic acid Following the procedure of Examples 1 and 2 except substituting the part B alcohol for [1β,2α(5Z),3α,4β]-7-[3-(hydroxymethyl)-7-oxabicyclo[2.2.1]hept-2-yl]-5-heptenoic acid, methyl ester, the title compound is obtained.

EXAMPLE 7

[1β,2α(5Z),3α,4β]-7-[3-[[[Oxo(phenylamino)acetyl]amino]butyl]-7-oxabicyclo[2.2.1]hept-2-yl]-5-heptenoic acid

A. [1β,2α(5Z),3α,4β]-7-[3-(3-Oxopropyl)-7-oxabicyclo[2.2.1]hept-2-yl]-5-heptenoic acid, methyl ester

[1β,2α(5Z),3α,4β]-7-[3-(2-Oxoethyl)-7-oxabicyclo[2.2.1]hept-2-yl]-5-heptenoic acid, methyl ester, is treated with methoxymethyltriphenylphosphonium chloride and potassium t-amylate as in Example 6. The product of this reaction is treated with aqueous trifluoroacetic acid to give [1β,2α(5Z),3α,4β]-7-[3-(3-oxopropyl)-7-oxabicyclo[2.2.1]hept-2-yl]-5-heptenoic acid, methyl ester (aldehyde A).

B. [1β,2α(5Z),3α,4β]-7-[3-(4-Oxobutyl)-7-oxabicyclo[2.2.1]hept-2-yl]-5-heptenoic acid, methyl ester Aldehyde A is treated as in part A above to yield the title B aldehyde [1β,2α(5Z),3α,4β]-7-[3-(4-oxobutyl)-7-oxabicyclo[2.2.1]hept-2-yl]-5-heptenoic acid, methyl ester.

C. [1β,2α(5Z),3α,4β]-7-[3-(Hydroxybutyl)-7-oxabicyclo[2.2.1]hept-2-yl]-5-heptenoic acid, methyl ester Following the procedure of Example 6 part B except substituting the Example 7 part B aldehyde for the Example 6 part A aldehyde, the title alcohol is obtained.

D. [1β,2α(5Z),3α,4β]-7-[3-[[[Oxo(phenylamino)acetyl]amino]butyl]-7-oxabicyclo[2.2.1]hept-2-yl]-5-heptenoic acid Following the procedure of Examples 1 and 2 except substituting the part C alcohol for [1β,2α(5Z),3α,4β]-7-[3-(hydroxymethyl)-7-oxabicyclo[2.2.1]hept-2-yl]-5-heptenoic acid, methyl ester, the title compound is obtained.

EXAMPLE 8

[1β,2α(5Z),3α,4β]-7-[3-[[[Oxo(ethylamino)acetyl]amino]methyl]-7-oxabicyclo[2.2.1]hept-2-yl]-5-heptenoic acid Following the procedure of Examples 1 and 2 except substituting ethylamine for aniline, the title compound is obtained.

EXAMPLE 9

[1β,2α(5Z),3α,4β]-7-[3-[[[Oxo(o-tolylamino)acetyl]amino]methyl]-7-oxabicyclo[2.2.1]hept-2-yl]-5-heptenoic acid Following the procedure of Examples 1 and 2 except substituting o-tolylamine for aniline, the title compound is obtained.

EXAMPLE 10

[1β,2α(5Z),3α,4β]-7-[3-[[[Oxo(benzylamino)acetyl]amino]methyl]-7-oxabicyclo[2.2.1]hept-2-yl]-5-heptenoic acid Following the procedure of Examples 1 and 2 except substituting benzylamine for aniline, the title compound is obtained.

EXAMPLE 11

[1β,2α(5Z),3α,4β]-7-[3-[[[Oxo(N-methyl propylamino)acetyl]amino]methyl]-7-oxabicyclo[2.2.1]-hept-2-yl]-5-heptenoic acid Following the procedure of Examples 1 and 2 except substituting N-methyl propylamine for aniline, the title compound is obtained.

EXAMPLE 12

[1β,2α(5Z),3α,4β]-7-[3-[[[Oxo(cyclohexylamino)acetyl]amino]methyl]-7-oxabicyclo[2.2.1]hept-2-yl]-5-heptenoic acid Following the procedure of Examples 1 and 2 except substituting cyclohexylamine for aniline, the title compound is obtained.

EXAMPLE 13

[1β,2α(5Z),3β,4β]-7-[3-[[[Oxo(propylamino)acetyl]amino]methyl]-7-oxabicyclo[2.2.1]hept-2-yl]-5-heptenoic acid Following the procedure of Examples 3 and 4 except substituting propylamine for aniline, the title compound is obtained.

EXAMPLE 14

[1β,2α(5Z),3β,4β]-7-[3-[[[Oxo(cyclopentylamino)acetyl]amino]methyl]-7-oxabicyclo[2.2.1-]hept-2-yl]-5-heptenoic acid Following the procedure of Examples 3 and 4 except substituting cyclopentylamine for aniline, the title compound is obtained.

EXAMPLE 15

[1β,2α(5Z),3β,4β]-7-[3-[[[Oxo(N-ethyl phenylamino)acetyl]amino]methyl]-7-oxabicyclo[2.2.1-]hept-2-yl]-5-heptenoic acid Following the procedure of Examples 3 and 4 except substituting N-ethyl phenylamine for aniline, the title compound is obtained.

EXAMPLE 16

[1β,2α(5Z),3β,4β]-7-[3-[[[Oxo(N-butyl methylamino)acetyl]amino]methyl]-7-oxabicyclo[2.2.1-]hept-2-yl]-5-heptenoic acid Following the procedure of Examples 3 and 4 except substituting N-butyl methylamine for aniline, the title compound is obtained.

EXAMPLE 17

[1β,2α(5Z),3β,4β]-7-[3-[[[Oxo(phenethylamino)acetyl]amino]methyl]-7-oxabicyclo[2.2.1]hept-2-yl]-5-heptenoic acid Following the procedure of Examples 3 and 4 except substituting phenethylamine for aniline, the title compound is obtained.

EXAMPLE 18

(1β,2β,3α,4β)-7-[3-[[[Oxo(dimethylamino)acetyl]amino]methyl]-7-oxabicyclo[2.2.1]hept-2-yl]heptanoic acid Following the procedure of Example 5, except substituting dimethylamine for aniline, the title compound is obtained.

EXAMPLE 19

(1β,2β,3α,4β)-7-[3-[[[Oxo(diphenylamino)acetyl]amino]methyl]-7-oxabicyclo[2.2.1]hept-2-yl]heptanoic acid Following the procedure of Example 5, except substituting diphenylamine for aniline, the title compound is obtained.

EXAMPLE 20

(1β,2β,3α,4β)-7-[3-[[[Oxo(N-benzyl ethylamino)acetyl]amino]methyl]-7-oxabicyclo[2.2.1-]hept-2-yl]heptanoic acid Following the procedure of Example 5, except substituting N-benzyl ethylamine for aniline, the title compound is obtained.

EXAMPLE 21

(1β,2β,3α,4β)-7-[3-[[[Oxo(cyclopropylmethylamino)acetyl]amino]methyl]-7-oxabicyclo[2.2.1-]hept-2-yl]heptanoic acid Following the procedure of Example 5, except substituting cyclopropylmethylamine for aniline, the title compound is obtained.

EXAMPLE 22

(1β,2β,3α,4β)-7-[3-[[[Oxo(N-cyclohexyl methylamino)acetyl]amino]methyl]-7-oxabicyclo[2.2.1-]hept-2-yl]heptanoic acid Following the procedure of Example 5, except substituting N-cyclohexyl methylamine for aniline, the title compound is obtained.

EXAMPLE 23

[1β,2α(5Z),3α,4β]-7-[3-[[[Oxo(ethylamino)acetyl]amino]ethyl]-7-oxabicyclo]2.2.1]hept-2-yl]-5-heptenoic acid Following the procedure of Example 6 except substituting ethylamine for aniline, the title compound is obtained.

EXAMPLE 24

[1β,2α(5Z),3α,4β]-7-[3-[[[Oxo(p-tolylamino)acetyl]amino]ethyl]-7-oxabicyclo[2.2.1]hept-2-yl]-5-heptenoic acid Following the procedure of Example 6 except substituting p-tolylamine for aniline, the title compound is obtained.

EXAMPLE 25

[1β,2α(5Z),3α,4β]-7-[3-[[[Oxo(benzylamino)acetyl]amino]ethyl]-7-oxabicyclo[2.2.1]hept-2-yl]-5-heptenoic acid Following the procedure of Example 6 except substituting benzylamine for aniline, the title compound is obtained.

EXAMPLE 26

[1β,2α(5Z),3α,4β]-7-[3-[[[Oxo(phenylpropylamino)acetyl]amino]ethyl]-7-oxabicyclo[2.2.1]hept-2-yl]-5-heptenoic acid Following the procedure of Example 6 except substituting phenylpropylamine for aniline, the title compound is obtained.

EXAMPLE 27

[1β,2α(5Z),3α,4β]-7-[3-[[[Oxo(N-ethyl hexylamino)acetyl]amino]ethyl]-7-oxabicyclo[2.2.1]hept-2-yl]-5-heptenoic acid Following the procedure of Example 6 except substituting N-ethyl hexylamine for aniline, the title compound is obtained.

EXAMPLE 28

[1β,2α(5Z),3α,4β]-7-[3-[[[Oxo(cyclopropylmethylamino)acetyl]amino]butyl]-7-oxabicyclo[2.2.1]hept-2-yl]-5-heptenoic acid Following the procedure of Example 7 except substituting cyclopropylmethylamine for aniline, the title compound is obtained.

EXAMPLE 29

[1β,2α(5Z),3α,4β]-7-[3-[[[Oxo(phenylbutylamino)acetyl]amino]butyl]-7-oxabicyclo[2.2.1]hept-2-yl]-5-heptenoic acid Following the procedure of Example 7 except substituting phenylbutylamine for aniline, the title compound is obtained.

EXAMPLE 30

[1β,2α(5Z),3α,4β]-7-[3-[[[Oxo(N-ethyl propylamino)acetyl]amino]butyl]-7-oxabicyclo[2.2.1]hept-2-yl]-5-heptenoic acid Following the procedure of Example 7 except substituting N-ethyl propylamine for aniline, the title compound is obtained.

EXAMPLE 31

[1β,2α(5Z),3α,4β]-7-[3-[[[Oxo(methylamino)acetyl]amino]butyl]-7-oxabicyclo[2.2.1]hept-2-yl]-5-heptenoic acid Following the procedure of Example 7 except substituting methylamine for aniline, the title compound is obtained.

EXAMPLE 32

[1β,2α(5Z),3α,4β]-7-[3-[[[Oxo(cyclopropylamino)acetyl]amino]butyl]-7-oxabicyclo[2.2.1]hept-2-yl]-5-heptenoic acid Following the procedure of Example 7 except substituting cyclopropylamine for aniline, the title compound is obtained.

EXAMPLE 33

[1β,2α(5Z),3α,4β]-7-[3-[[(Oxamyl)amino]methyl]-7-oxabicyclo[2.2.1]hept-2-yl]-5-heptenoic acid Following the procedure of Examples 1 and 2 except substituting oxamic acid in Example 1 part D for phenyloxamic acid, the title compound is obtained.

EXAMPLE 34

[1β,2α(5Z),3β,4β]-7-[3-[[(Oxamyl)amino]methyl]-7-oxabicyclo[2.2.1]hept-2-yl]-5-heptenoic acid Following the procedure of Examples 3 and 4 except substituting oxamic acid in Example 1 part D for phenyloxamic acid, the title compound is obtained.

EXAMPLE 35

(1β,2β,3α,4β)-7-[3-[[(Oxamyl)amino]methyl]-7-oxabicyclo[2.2.1]hept-2-yl]heptanoic acid Following the procedure of Examples 5, 1 and 2 except substituting oxamic acid in Example 1 part D for phenyloxamic acid, the title compound is obtained.

EXAMPLE 36

[1β,2α(5Z),3α,4β]-7-[3-[[(Oxamyl)amino]ethyl]-7-oxabicyclo[2.2.1]hept-2-yl]-5-heptenoic acid Following the procedure of Examples 6, 1 and 2 except substituting oxamic acid in Example 1 part D for phenyloxamic acid, the title compound is obtained.

EXAMPLE 37

[1β,2α(5Z),3α,4β]-7-[3-[[(Oxamyl)amino]butyl]-7-oxabicyclo[2.2.1]hept-2-yl]-5-heptenoic acid Following the procedure of Examples 7, 1 and 2 except substituting oxamic acid in Example 1 part D for phenyloxamic acid, the title compound is obtained.

What is claimed is:

1. A compound having the structural formula

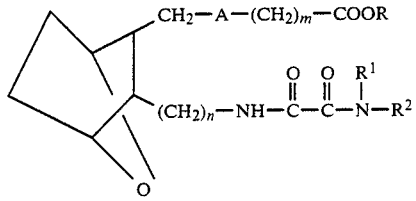

and including all stereoisomers thereof wherein
A is —CH=CH— or —(CH$_2$)$_2$—;
m is 1 to 8; n is 1 to 5;
R is hydrogen, lower alkyl or alkali metal;
R$^1$ and R$^2$ are the same or different and are selected from the group consisting of hydrogen, lower alkyl, aryl, aralkyl and cycloalkyl, wherein the term lower alkyl or alkyl by itself or as part of another group contains 1 to 12 carbons and is unsubstituted or substituted with halo, trifluoromethyl, alkoxy, aryl, alkyl-aryl, haloaryl, cycloalkyl or alkylcycloalkyl;
the term aryl by itself or as part of another group contains 6 to 10 carbons and is unsubstituted or substituted with lower alkyl, halogen or lower alkoxy;
the term cycloalkyl by itself or as part of another group contains 3 to 12 carbons and is unsubstituted or substituted with 1 or 2 halogens, 1 or 2 lower alkyl groups and/or 1 or 2 lower alkoxy groups, and the terms $(CH_2)_m$ and $(CH_2)_n$ may be unsubstituted or include one or more lower alkyl substituents.

2. THe compound as defined in claim 1 wherein R is H or $CH_3$.

3. The compound as defined in claim 1 wherein A is —CH=CH—.

4. The compound as defined in claim 1 wherein A is —CH=CH—, m is 2 to 4, n is 1 to 3, R is H or $CH_3$, $R^1$ is H and $R^2$ is lower alkyl or aryl.

5. The compound as defined in claim 1 wherein A is —CH=CH—, m is 3, n is 1, R is H, $R^1$ is H and $R^2$ is lower alkyl or phenyl.

6. The compound as defined in claim 1 having the name [1β,2α(5Z),3α,4β]-7-[3-[[[oxo(phenylamino)acetyl]amino]methyl]-7-oxabicyclo[2.2.1-]hept-2-yl]-5-heptenoic acid or its methyl ester, and including all stereoisomers thereof.

7. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

8. The method as defined in claim 7 wherein said compound is administered in an amount within the range of from about 1 to about 100 mg/kg.

9. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

10. A method of inhibiting platelet aggregation which comprises administering to a mammalian host an effective amount of a compound as defined in claim 1 or a pharmaceutically acceptable salt thereof.

11. A method of inhibiting bronchoconstriction associated with asthma, which comprises administering to a mammalian host an effective amount of a compound as defined in claim 1 or a pharmaceutically acceptable salt thereof.

* * * * *